United States Patent [19]

Hester

[11] Patent Number: 5,686,384
[45] Date of Patent: Nov. 11, 1997

[54] COMPATIBILITY AGENT AND METHOD

[75] Inventor: Dennis M. Hester, Richmond, Calif.

[73] Assignee: Zeneca Limited, London, England

[21] Appl. No.: 403,592

[22] Filed: Mar. 14, 1995

[51] Int. Cl.$^6$ .......................... A01N 25/32; A01N 57/04
[52] U.S. Cl. .......................... 504/116; 504/127; 504/103; 504/206; 71/DIG. 1
[58] Field of Search .......................... 504/116, 206, 504/127, 103; 71/DIG. 1

[56] References Cited

U.S. PATENT DOCUMENTS

| | | | |
|---|---|---|---|
| 4,270,916 | 6/1981 | Racciato | 8/527 |
| 4,446,042 | 5/1984 | Leslie | 252/102 |
| 4,966,728 | 10/1990 | Hazen | 252/354 |
| 5,084,087 | 1/1992 | Hazen et al. | 71/123 |
| 5,260,260 | 11/1993 | Gednalske et al. | 504/206 |

OTHER PUBLICATIONS

BASF Technical Sheet, "Pluronic and Tetronic Surfactants", BASF Corp., 1989.

*Primary Examiner*—Jose' G. Dees
*Assistant Examiner*—Brian G. Bembenick
*Attorney, Agent, or Firm*—Joseph R. Snyder

[57] ABSTRACT

A compatibility agent comprising a block copolymer of ethylene oxide and propylene oxide comprising about 30–80% ethylene oxide and about 20–70% propylene oxide which has been found useful for making pesticidal compositions compatible when combined.

10 Claims, No Drawings

COMPATIBILITY AGENT AND METHOD

TECHNICAL FIELD

The present invention relates to a compatibility agent, more particularly to a compatibility agent which renders compatible a mixture of formulated pesticidal compositions, wherein at least one formulated pesticidal composition contains an anionic surfactant, and at least one formulated pesticidal composition contains a cationic surfactant.

BACKGROUND AND PRIOR ART

Farmers find it desirable to tank mix formulated commercial herbicides in the field. The reasons for this desirability may include a need to enhance efficacy through a synergistic response, or the desire to control different kinds of weeds. In addition, mixing formulated herbicides may allow greater weed control, while overall using less active ingredients. Further, it might be desirable to tank mix a formulated insecticide, or other pesticides, with a formulated herbicide. In short, the greater flexibility to tank mix formulated products, the more ability a farmer has to adapt available resources to combat new and existing problems.

Formulated pesticidal mixtures comprising two different active ingredients, wherein one of the commercial formulations contain a cationic surfactant and the other contains an anionic surfactant, can present a special problem. Sometimes said mixtures result in formation of a precipitate or sediment due to the incompatibility of the surfactants. The resulting precipitates make spraying the mixtures quite problematic. Agglomerated mixtures do not flow properly, and tend to clog spray rigs, hoses and nozzles. The term pesticide may include herbicide, insecticide, fungicide or biocide.

U.S. Pat. No. 4,446,042 describes an invention which relates to laundry detergent compositions containing nonionic surfactants, quaternary ammonium cationic surfactants and selected anionic brighteners. The selection of suitable brighteners for detergents containing nonionic and cationic surfactants is problematic since many conventional brighteners are anionic in nature and tend to form insoluble complexes with the quaternary ammonium cationic surfactants. This surfactant compatibility problem is discussed and solved with certain stilbene disulfonate anionic brighteners.

Another area where this type of compatibility problem exists is in the area of dyeing or printing. In U.S. Pat. No. 4,270,916 cationic or certain anionic dyes are rendered compatible with normally incompatible anionic polymers by the addition of nonionic, amphoteric or anionic surface active agents. Examples of such polymers are algin, xanthan gum, S-7 gum polyacrylic acid or polymethacrylic acid. Among the various types of nonionic detergents are condensation products of ethylene oxide with fatty acids, condensation products of ethylene oxide with fatty alcohols, condensation products of ethylene oxide with fatty amines or fatty amides and condensation products of ethylene oxide with phenolic compounds. Among the various anionic surfactants are aliphatic fatty condensate with ethylene oxide, the sodium salt of oleyl sarcoside and condensation product of fatty acids and proteins.

U.S. Pat. No. 4,966,728 relates to adjuvants for postemergent herbicides which are crop oil concentrates. The crop oil concentrates of that invention enhance the activity obtained with other commercial adjuvants. The adjuvant mixtures are suitable for cyclohexanone-type herbicides. The crop oil concentrates of that invention comprise, a mixture of: a) a first active component which is a low foaming nonionic surfactant; b) an anionic surfactant derived from esterification of a polyoxyalkylene nonionic surfactant with a dihydric or trihydric inorganic acid or by carboxylation with an organic acid derivative; and c) optionally a third active component which is a lower alkanol ester of a long chain fatty acid and d) a fourth component of a hydrocarbon "oil".

U.S. Pat. No. 5,084,087 describes an invention relating to adjuvants for postemergent herbicides which fall into the category of crop oil concentrates. The crop oil concentrates of that invention comprise a mixture of: a) one or more herbicides selected from the group consisting of diphenylether herbicides, phenoxyphenoxy herbicides, imidazoline herbicides and cyclohexenone herbicides b) an emulsifier component which is a combination of (i) a polyoxyalkylene nonionic surfactant having an HLB of from 10 to 14 and (ii) an anionic surfactant selected from the group consisting of the dialkyl metal sulfosuccinates and the metal alkylbenzene sulphonates; c) optionally a second surface active component which is a low foaming polyoxyalkylene nonionic surfactant having an HLB of less than 10; and d) a lower alkanol ester of a long chain fatty acid. As an additional component, a hydrocarbon oil may be added.

The present invention relates to the addition of a nonionic surfactant, also called a compatibility agent, which renders compatible mixtures of normally incompatible formulated pesticides, preferably herbicides. It is an object of the present invention to provide an agent for making combined pesticidal compositions compatible, said composition comprising at least one formulated pesticidal composition containing a cationic surfactant, and at least one formulated pesticidal composition containing an anionic surfactant. Another object of the present invention is to prevent the formation of a precipitate or sediment in mixtures of pesticides containing cationic and anionic surfactants normally incompatible with each other. A further object is to provide a stable pesticidal mixture containing at least one cationic surfactant and at least one anionic surfactant. A still further object of the present invention is a method of controlling undesirable vegetation with said combined compatible pesticidal compositions.

SUMMARY OF INVENTION

One aspect of this invention relates to a compatibility agent which renders compatible, mixtures of normally incompatible formulated pesticides, and more specifically, the use of a compatibility agent comprising:

a block copolymer of ethylene oxide and propylene oxide comprising about 30–80% ethylene oxide and about 20–70% propylene oxide. In one aspect this invention comprises a compatibility agent comprising:
  a) a block copolymer of ethylene oxide and propylene oxide comprising about 30–80% ethylene oxide and about 20–70% propylene oxide;
  b) an antifoaming agent; and
  c) an antifreeze agent.

Another aspect of this invention relates to a pesticidal composition wherein the compatibility agent and more particularly the block copolymer component of it is combined with, or incorporated into, a pesticidal composition containing an anionic or cationic surfactant.

In still another aspect, this invention relates to a combined pesticidal composition, comprising:
  a) a block copolymer of ethylene oxide and propylene oxide comprising about 30–80% ethylene oxide and about 20–70% propylene oxide;

b) a first formulated pesticidal composition containing a cationic surfactant; and c) a second formulated pesticidal composition containing an anionic surfactant.

DETAILED DESCRIPTION OF THE INVENTION

It has now been found that combined formulated pesticidal compositions, preferably herbicidal compositions, comprising at least one formulated pesticidal composition having a cationic surfactant, and at least one formulated composition having an anionic surfactant, that are normally incompatible with each other, are rendered compatible by the presence of a nonionic surfactant. In general, pesticidal active ingredients are not applied to the locus of the pests alone. Normally these active ingredients are applied in combination with surface active agents, wetting agents, solvents, oils, carriers or diluents or mixtures thereof. The term "formulated pesticidal compositions" refers to compositions containing an active ingredient(s) and one or more of these other inert ingredients.

In some aspects of this invention, the compatibility agent will be combined with, or incorporated into a formulated pesticidal composition containing the cationic or anionic surfactant. In other aspects, the compatibility agent will be separate in order that it may be used in tank mixes in the field. In still other aspects of the invention, the compatibility agent may be combined with formulated pesticidal compositions containing cationic, nonionic or amphoteric surfactants or mixtures thereof.

It has now been surprisingly found that certain nonionic surfactants act as effective compatibility agents of combined pesticidal compositions. The nonionic surfactants useful as compatibility agents are nonionic water soluble block copolymers of ethylene oxide and propylene oxide. These surfactants have about 30–80% ethylene oxide and about 20–70% propylene oxide content, preferably about 30–50% ethylene oxide and about 50–70% propylene oxide content, and most preferably about 70% ethylene oxide and about 30% propylene oxide content. The average molecular weight is between 5000–15,000 g/mole, preferably about between 4900 to 6500 g/mole, and most preferably about 12,000–13,000 g/mole. The hydrophile-lipophile balance (HLB) is about 7 to 23, preferably 7–18, and most preferably 18–23. The preferred nonionic surfactants acting as compatibility agents are Pluronic P-103®, Pluronic P-104®, Pluronic P-105®, Pluronic F-108® and Pluronic F-127®, which are available from BASF.

CATIONIC SURFACTANTS

Among the various cationic surfactants which are rendered compatible with anionic surfactants, with the addition of the nonionic compatibility agent of this invention, include ethoxylates of tallow amine. The term "tallow" refers to alkyl groups derived from tallow fatty acids. Other cationic surfactants are Ethoquad C/25, which may be described as methylpolyoxyethylene (15) coco-ammonium chloride, Ethoquad C/12, which may be described as methylbis(2-hydroxyethyl) coco-ammonium chloride, and Duoquad T-50, which may be described as a diquaternary ammonium salt, all available from Akzo Chemie America. The term "coco" refers to alkyl groups derived from coconut fatty acids. This list is not intended to be exhaustive, but other cationic surfactants will be apparent to those skilled in the art.

A commercial herbicide containing a cationic surfactant, made compatible with various anionic surfactants by the compatibility agent of this invention is Roundup®. The active ingredient in Roundup® is N-phosphonomethylglycine isopropylamine salt. It is available from Monsanto Co.

ANIONIC SURFACTANTS

Among the anionic surfactants which have been found compatible with the above cationic surfactants using the compatibility agent, are alkylaryl sulfonate salts, preferably the calcium salts, although the alkali metal salts and other alkaline earth metal salts may be used. Most preferred is calcium dodecylbenzene sulfonate. A commercial herbicide containing an alkylbenzene sulfonate salt surfactant is Surpass®-100, available from Zeneca Agrochemicals. The active ingredient in Surpass®-100 is 2-chloro-N-ethoxymethyl-6-ethylacet-o-toluidide, commonly known as acetochlor.

Acetochlor is a member of the acetanilide class of herbicides. Alachlor is another acetanilide herbicide. Other acetanilide herbicides are known to those skilled in the art.

OPTIONAL COMPONENTS

In addition to the nonionic surfactant, there are other ingredients which may be added to affect different properties of the compatibility agent. For instance, an antifoaming or defoaming agent may be added. Nonionic surfactants which are block copolymers may be used as antifoaming agents. A preferred antifoaming agent is Pluronic L-61®. Pluronic L-61® is a block copolymer of ethylene oxide and propylene oxide available from BASF. The propylene oxide content is approximately 10%.

In addition to antifoaming agents, antifreeze agents such as propylene glycol, ethylene glycol, isopropyl alcohol, urea ammonium nitrate and other salts. This list is not meant to be exhaustive, but those skilled in the art will know of other freezing point depressants.

Further, biocides may be included to prevent the degradation of the surfactants by microbes. The Proxel® series are typical examples of suitable biocides and they are available from ICI Americas. Other biocides will be known to those skilled in the art.

COMPATIBILITY TEST

The test used to establish compatibility may be performed in a graduated cylinder. This test involves mixing the components in the following order: a formulated pesticidal composition containing an anionic surfactant, the compatibility agent and finally a formulated pesticidal composition containing a cationic surfactant. The cylinder is inverted several times to agitate and mix the ingredients.

An acceptable result in the graduated cylinder test is evidenced by the absence of flocculation or sediment, or if flocculation or sediment is present it must be capable of being easily dispersed upon agitation or mixing. Flocculation which results in a hard pack sediment or soft flocculation which agglomerates will give unacceptable results. Solutions where there is neither flocculation nor sediment, or solutions where the flocculation is easily dispersed are poured through a 100 mesh sieve. To be acceptable, there must be little or no residue present when the solution is passed through the sieve. Mixtures which leave little or no residue on the sieve are subjected to a more rigorous tank mix test with a three gallon spray rig.

The three gallon spray rig is composed of a square tank with a three gallon capacity. The tank is fitted with a recirculation pump which draws fluid from the bottom center of the tank. The inlet for the tank is a "t-shaped" nozzle located in the center of the tank approximately one inch from the bottom which provides agitation for the solution. The recirculation pump is fitted with a pressure regulator, a 50 mesh in-line screen and a spray nozzle.

The procedure for conducting a tank mix test in the three gallon rig is to first add water to the one and one half gallon level and start the recirculation. The pressure regulator is adjusted to 45–50 psi. Atrazine is added to the tank and allowed to disperse completely, which typically takes 30–60 seconds. Next, the formulated pesticidal product containing an anionic surfactant, such as Surpass®-100, is added and allowed to disperse completely. This typically takes 30–60 seconds. The compatibility agent is then added and allowed to disperse completely. This usually takes 30–60 seconds. Any remaining tank mix components are added, with the order of addition generally not being important. Water is added to the three gallon level and the solution is allowed to recirculate for 10 minutes. The recirculation is stopped and the solution is allowed to stand undisturbed for 20 minutes. The level of flocculation or sediment is noted and the contents recirculated for 10 additional minutes. If flocculation or sediment is observed, the ease with which it disperses is noted. The solution is then sprayed through a common spray nozzle and screen into a holding vessel.

The inside of the tank is inspected for residue on the sides and bottom. The 50 mesh in-line sieve is inspected for residue and the spray nozzle is disassembled and inspected for residue. A showing of trace amounts of residue on the inside of the tank, the in-line sieve, or the spray nozzle is indicative of a satisfactory result. The solution in the holding vessel is returned to the tank and allowed to stand for 2 hours. The inspection procedure is repeated and noted. The solution is allowed to stand undisturbed overnight. Little or no residue on the inside of the tank is indicative of a satisfactory result.

The following nonlimiting examples illustrate the present invention:

EXAMPLE 1

A two-gallon nonionic compatibility solution for the three-gallon spay rig was prepared using the following ingredients which were mixed in the order indicated:

| Ingredient | Weight % | Weight (grams) | Order of Addition |
| --- | --- | --- | --- |
| Pluronic F-127 ® | 10% | 750.0 | 4 |
| Pluronic L-61 ® | 0.5% | 37.5 | 3 |
| Propylene glycol | 15% | 1125.0 | 2 |
| water | 74.5% | 5587.5 | 1 |

The ingredients were mixed in a one-half gallon glass jug and combined enough times to obtain two gallons total. The solution was heated to about 50° C. and allowed to stir until the Pluronic F-127® was completely dissolved. This procedure was repeated until a total of two gallons was present. The above compatibility reagent was added to the following combination of ingredients in the following order:

| Ingredient | Amount | Order of Addition |
| --- | --- | --- |
| Atrazine-90 DF | 120 grams | 1 |
| Surpass ®-100 | 902 mL | 2 |

-continued

| Ingredient | Amount | Order of Addition |
| --- | --- | --- |
| Compatibility Agent | 45 mL | 3 |
| Ambush ® 2-E | 53 mL | 4 |
| Weedone-638 ® | 53 mL | 5 |
| Roundup ® | 141 mL | 6 |

Ambush® is a trademark for permethrin available from Zeneca Ag Products. Atrazine-90 DF is a water dispersible granule available from Sostram. The mixture in the above example did not precipitate or agglomerate, and gave satisfactory results in the three-gallon spray rig.

EXAMPLE 2

The compatibility agent in Example 1 was used to make compatible the following normally incompatible mixture. The ingredients were added in the following order to a graduated cylinder:

| Ingredient | Amount | Order of Addition |
| --- | --- | --- |
| Surpass ®-100 | 6.5 mL | 1 |
| Compatibility Agent | 0.4 mL | 2 |
| Weedone-638 ® | 0.48 mL | 3 |

Weedone-638® is a commercial herbicidal product, the active ingredient of which is 2,4 dichlorophenoxyacetic acid; it is available from Rhone-Poulenc Agrochimie. The mixture in the above example did not precipitate or agglomerate.

EXAMPLE 3

The compatibility agent in Example 1 was used to make compatible the following normally incompatible mixture. The ingredients were added in the following order into the three gallon spray rig:

| Ingredient | Amount | Order of Addition |
| --- | --- | --- |
| DoublePlay ™ | 851 mL | 3 |
| Compatibility Agent | 29 mL | 2 |
| Bladex ® | 302 grams | 1 |

The mixture in the above example did not precipitate or agglomerate. Bladex®, which is available from DuPont, is a commercial formulation of 2-[[4-chloro-6-(ethylamino)-1,3, 5-triazin-2-yl]amino]-2-methylpropionitrile, commonly known as cyanazine. DoublePlay™ is a commercial herbicide available from Zeneca Agrochemicals. The active ingredients in DoublePlay™ are S-ethyl dipropylthiocarbamate, commonly known as EPTC and acetochlor. DoublePlay™ contains the surfactant AL2757, available from ICI Americas Inc.

EXAMPLE 4

This example compares the results of a solution without the addition of a compatibility agent (Part A) versus a solution with the addition of a compatibility agent (Part B).

Part A

To a graduated cylinder was added 7.48 grams Surpass®-100 dissolved in 90 mL of water followed by 0.2 grams of Ethoquad C/25. The mixture was dispersed completely. The cylinder was allowed to stand for 30 minutes. Flocculation and sedimentation were noted and re-dispersed. The contents of the cylinder were then passed through a 100 mesh sieve.

| Ingredient | Amount | Order of Addition |
|---|---|---|
| Surpass ®-100 | 7.48 grams | 2 |
| Water | 90 mL | 1 |
| Ethoquad C/25 | 0.2 grams | 3 |

Without the addition of a compatibility agent, 15 mL of flocculate appeared at the top and 15 mL of flocculate appeared at the bottom (30 mL total) and a major sediment was left on the 100 mesh sieve.

Part B

To a graduated cylinder was added 7.48 grams Surpass®-100 dissolved in 90 mL of water followed by the addition of the compatibility agent in Example 1 (0.44 grams) and finally 0.2 grams of Ethoquad C/25. The mixture was dispersed completely. The cylinder was allowed to stand for 30 minutes. Flocculation and sedimentation were noted and re-dispersed. The contents of the cylinder were then passed through a 100 mesh sieve.

| Ingredient | Amount | Order of Addition |
|---|---|---|
| Surpass ®-100 | 7.48 grams | 2 |
| Water | 90 mL | 1 |
| Compatibility Agent | 0.44 grams | 3 |
| Ethoquad C/25 | 0.2 grams | 4 |

With the addition of the compatibility agent in Example 1 there appeared 15 mL of flocculate at the top of the cylinder which readily disperses. No flocculate appeared at the bottom of the cylinder and a very minor amount of sediment on the 100 mesh sieve.

EXAMPLE 5

To a graduated cylinder was added 7.48 grams Surpass®-100 dissolved in 90 mL of water followed by the addition of 0.44 grams of a compatibility agent. The mixture was completely dispersed and then 0.2 grams of Ethoquad C/25 was added. The mixture was again dispersed completely. The cylinder was allowed to stand for 30 minutes. Flocculation and sedimentation were noted and re-dispersed. The contents of the cylinder were then passed through a 100 mesh sieve.

| Ingredient | Amount | Order of Addition |
|---|---|---|
| Surpass ®-100 | 7.48 grams | 2 |
| Water | 90 mL | 1 |
| Compatibility Agent | 0.44 grams | 3 |
| Ethoquad C/25 | 0.2 grams | 4 |

The compatibility agent comprised 10% by weight Pluronic P-103®, 0.5% by weight Pluronic L-61®, 15% by weight Propylene glycol, and 74.5% by weight water. There appeared 3 mL of flocculate at the top of the cylinder which readily disperses, no flocculate at the bottom and a minor amount of sediment on the 100 mesh sieve.

EXAMPLE 6

To a graduated cylinder was added 7.48 grams Surpass®-100 dissolved in 90 mL of water followed by the addition of 0.44 grams of a compatibility agent. The mixture was completely dispersed and then 0.2 grams of Ethoquad C/25 was added. The mixture was again dispersed completely. The cylinder was allowed to stand for 30 minutes. Flocculation and sedimentation were noted and re-dispersed. The contents of the cylinder were then passed through a 100 mesh sieve.

| Ingredient | Amount | Order of Addition |
|---|---|---|
| Surpass ®-100 | 7.48 grams | 2 |
| Water | 90 mL | 1 |
| Compatibility Agent | 0.44 grams | 3 |
| Ethoquad C/25 | 0.2 grams | 4 |

The compatibility agent comprised, 10% by weight Pluronic P-104®, 0.5% by weight Pluronic L-61®, 15% by weight Propylene glycol, and 74.5% by weight water. There was no flocculate at the top or bottom of the cylinder and a minor amount of sediment on the 100 mesh sieve.

EXAMPLE 7

To a graduated cylinder was added 7.48 grams Surpass®-100 dissolved in 90 mL of water followed by the addition of 0.44 grams of a compatibility agent. The mixture was completely dispersed and then 0.2 grams of Ethoquad C/25 was added. The mixture was again dispersed completely. The cylinder was allowed to stand for 30 minutes. Flocculation and sedimentation were noted and re-dispersed. The contents of the cylinder were then passed through a 100 mesh sieve.

| Ingredient | Amount | Order of Addition |
|---|---|---|
| Surpass ®-100 | 7.48 grams | 2 |
| Water | 90 mL | 1 |
| Compatibility Agent | 0.44 grams | 3 |
| Ethoquad C/25 | 0.2 grams | 4 |

The compatibility agent comprised, 10% by weight Pluronic P-105®, 0.5% by weight Pluronic L-61®, 15% by weight Propylene glycol, and 74.5% by weight water. There was no flocculate at the top or bottom of the cylinder and a minor amount of sediment on the 100 mesh sieve.

What is claimed is:

1. A combined pesticidal composition comprising:
    a) a block copolymer of ethylene oxide and propylene oxide comprising about 30–80% ethylene oxide and about 20–70% propylene oxide;
    b) a first formulated pesticidal composition containing a cationic surfactant;
    c) a second formulated pesticidal composition containing an anionic surfactant; wherein said first and second pesticidal compositions are incompatible in the absence of said block copolymer and compatible in the presence of said block copolymer.

2. A combined pesticidal composition according to claim 1, wherein said block copolymer of ethylene oxide and propylene oxide comprises about 30–50% ethylene oxide and about 50–70% propylene oxide.

3. A combined pesticidal composition according to claim 1, wherein said block copolymer of ethylene oxide and propylene oxide comprises about 70% ethylene oxide and about 30% propylene oxide.

4. A combined pesticidal composition according to claim 1, wherein said first formulated pesticidal composition comprises an herbicide.

5. A combined pesticide composition according to claim 1, wherein said second formulated pesticidal composition comprises an herbicide.

6. A combined pesticidal composition according to claim 4, wherein said herbicide comprises an N-phosphonomethylglycine salt.

7. A combined pesticidal composition according to claim 5, wherein said herbicide comprises an acetanilide.

8. A combined pesticidal composition according to claim 7, wherein said acetanilide comprises acetochlor.

9. A combined pesticidal composition according to claim 1, wherein the composition is a liquid.

10. A method for controlling undesirable vegetation, comprising: applying to said vegetation or the locus thereof, a pesticidal effective amount of a composition according claim 1.

* * * * *